US011543395B2

(12) United States Patent
Nakashima

(10) Patent No.: US 11,543,395 B2
(45) Date of Patent: Jan. 3, 2023

(54) INFORMATION PROCESSING DEVICE, INFORMATION PROCESSING METHOD, AND INFORMATION PROCESSING PROGRAM

(71) Applicant: Shimadzu Corporation, Kyoto (JP)

(72) Inventor: Minori Nakashima, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 334 days.

(21) Appl. No.: 16/098,200

(22) PCT Filed: Jun. 22, 2016

(86) PCT No.: PCT/JP2016/068505
§ 371 (c)(1),
(2) Date: Nov. 1, 2018

(87) PCT Pub. No.: WO2017/221344
PCT Pub. Date: Dec. 28, 2017

(65) Prior Publication Data
US 2019/0178857 A1    Jun. 13, 2019

(51) Int. Cl.
*G01N 30/86* (2006.01)
*G01N 30/88* (2006.01)
*G01N 33/02* (2006.01)

(52) U.S. Cl.
CPC ......... *G01N 30/8679* (2013.01); *G01N 30/88* (2013.01); *G01N 33/02* (2013.01);
(Continued)

(58) Field of Classification Search
CPC .............. G01N 30/8679; G01N 30/88; G01N 30/8872; G01N 33/02; G01N 2030/8813
See application file for complete search history.

(56) References Cited

U.S. PATENT DOCUMENTS

2004/0096982 A1\* 5/2004 Barnea .................. G16C 20/20
436/173
2005/0051466 A1\* 3/2005 Carter .................. G01N 15/042
210/94
(Continued)

FOREIGN PATENT DOCUMENTS

JP       2002-350426 A    12/2002
JP       2015-025680 A     2/2015

OTHER PUBLICATIONS

International Search Report and Written Opinion dated Sep. 27, 2016 of corresponding International Application No. PCT/JP2016/068505; 10 pgs.
(Continued)

*Primary Examiner* — Son T Le
*Assistant Examiner* — Lal C Mang
(74) *Attorney, Agent, or Firm* — Maier & Maier, PLLC

(57) ABSTRACT

An information processing device processes information based on a plurality of chromatograms obtained by analyzing a plurality of samples. A determination processing unit determines presence or absence of each of a plurality of target components in each sample based on the plurality of chromatograms. A list generation processing unit generates a list associating the plurality of target components with each sample and indicating the presence or absence of each of the plurality of target components in each sample determined by the determination processing unit. Checking the list enables prompt confirmation of the presence or absence of the target components in each of the plurality of samples.

17 Claims, 5 Drawing Sheets

(52) U.S. Cl.
CPC .............. *G01N 2030/8813* (2013.01); *G01N 2030/8872* (2013.01)

(56) References Cited

U.S. PATENT DOCUMENTS

| | | | | |
|---|---|---|---|---|
| 2010/0264332 | A1* | 10/2010 | Coker | G01N 21/65 250/459.1 |
| 2010/0288918 | A1* | 11/2010 | Satulovsky | B01D 59/44 250/282 |
| 2012/0070516 | A1* | 3/2012 | Tranquil | A01N 65/34 424/735 |
| 2013/0244272 | A1* | 9/2013 | Moularat | G01N 27/62 435/34 |
| 2014/0257712 | A1* | 9/2014 | Mito | G01N 30/74 702/25 |
| 2015/0198569 | A1* | 7/2015 | Baba | G01N 30/72 250/282 |
| 2015/0318154 | A1* | 11/2015 | Campbell | H01J 49/022 250/282 |
| 2017/0099862 | A1* | 4/2017 | Binder | A23L 5/23 |

OTHER PUBLICATIONS

Agilent Open LAB Intelligence Report, Agilent Technologies Inc. [online], Apr. 1, 2016, pp. 6 to 11, [retrieval date Sep. 7, 2016], URL: http://www.chem-agilent.com/pdf/5991-6805 lo. pdf, 22 pgs including English-language partial translation.

GCMSSolution Sosa no Q&A, Shimadzu Corp. [online], Jul. 14, 2010, entire text, [retrieval date: Sep. 7, 2016], URL:http://www.an.shimadzu. co.jp/gcms/support/faq/gcmssol/faq9.htm, 62 pgs.

Shokuhinchu Zanryu Noyaku no Kenshutsu Kagen o Hikisageru Atarashii Agilent 7000C Triple Shijukyoku GC/MS System, Access Agilent, Agilent Technologies Inc. [online], Jan. 2014, [retrieval date: Sep. 7, 2016], URL:http://www.chem-agilent.com/access agilent/article.php?page=201401-04, 6 pgs.

Shen Xiaofeng, "Use Empower 3 software to Improve work efficiency," Waters (Science and Technology), Shanghai Co., Ltd. Jul. 23, 2014. Website. Retrieved from: www.docin.com/P-87109813.html (22 pp., including machine-generated English translation).

Li Hongwei, "Overview of relevant substance Inspection methods," Dec. 3, 2015. Website. Retrieved from http://wenku.baidu.com/view/12b054d95acfalc7ab00cca1.html (3 pp., including machine-generated English translation).

Chinese Office Action dated Apr. 13, 2020, in connection with corresponding CN Application No. 201680086935.3 (18 pp., including machine-generated English translation).

* cited by examiner

FIG. 2

| | | | | | | | | | |
|---|---|---|---|---|---|---|---|---|---|
| OVERALL DETERMINATION | Fail | | | | | | | | |

| | |
|---|---|
| DEVICE NAME | Nexera-i 3D |
| ANALYST | System Administrator |
| ANALYSIS DATE/TIME | 2016/1/12 21:06:40 |

CONCENTRATION (μg/kg)

| DATA FILE NAME | DETERMINATION | Total Aflatoxin | | Aflatoxin B1 | | Aflatoxin B2 | | Aflatoxin G1 | | Aflatoxin G2 | | Zearalenone | | Ochratoxin A | | Deoxy-nivalenol | | Nivalenol | |
|---|---|---|---|---|---|---|---|---|---|---|---|---|---|---|---|---|---|---|---|
| Sample_001.lcd | Pass | ○ | N.D. | ○ | N.D. | ○ | N.D. | ○ | N.D. | ○ | N.D. | ○ | N.D. | ○ | N.D. | ○ | N.D. | ○ | N.D. |
| Sample_002.lcd | Pass | ○ | N.D. | ○ | N.D. | ○ | N.D. | ○ | N.D. | ○ | N.D. | ○ | N.D. | ○ | N.D. | ○ | N.D. | ○ | N.D. |
| Sample_003.lcd | Pass | ○ | N.D. | ○ | N.D. | ○ | N.D. | ○ | N.D. | ○ | N.D. | ○ | N.D. | ○ | N.D. | ○ | N.D. | ○ | N.D. |
| Sample_004.lcd | Pass | ○ | N.D. | ○ | N.D. | ○ | N.D. | ○ | N.D. | ○ | N.D. | ○ | N.D. | ○ | N.D. | ○ | N.D. | ○ | N.D. |
| Sample_006.lcd | Fail | ○ | N.D. | ○ | N.D. | ○ | N.D. | ○ | N.D. | ○ | N.D. | ○ | N.D. | ○ | N.D. | × | 806.27 | △ | 462.60 |
| Sample_007.lcd | Pass | ○ | N.D. | ○ | N.D. | ○ | N.D. | ○ | N.D. | ○ | N.D. | ○ | N.D. | ○ | N.D. | ○ | N.D. | ○ | N.D. |
| Sample_008.lcd | Pass | ○ | N.D. | ○ | N.D. | ○ | N.D. | ○ | N.D. | ○ | N.D. | ○ | N.D. | ○ | N.D. | ○ | N.D. | ○ | N.D. |
| Sample_009.lcd | Fail | × | 4.57 | × | 1.10 | × | 1.13 | × | 1.17 | × | 1.17 | △ | 17.63 | △ | 1.50 | ○ | N.D. | △ | 418.17 |
| Sample_010.lcd | Caution | ○ | N.D. | ○ | N.D. | ○ | N.D. | ○ | N.D. | ○ | N.D. | ○ | N.D. | ○ | N.D. | △ | 484.31 | ○ | N.D. |
| QUANTITATIVE LOWER LIMIT | | 4.00 | | 0.04 | | 0.04 | | 0.01 | | 0.09 | | 0.01 | | 1.75 | | 0.04 | | 70.00 | |
| SET REFERENCE VALUE | | 4.00 | | 1.00 | | 1.00 | | 1.00 | | 1.00 | | 20.00 | | 2.00 | | 500.00 | | 500.00 | |
| COLLECTION RATE OF SOFT WHEAT FLOUR (%) | | 90 | | 90 | | 90 | | 90 | | 90 | | 70 | | 70 | | 70 | | 70 | |

210 — [2016/5/15 10:22:31 : CHECKED[User 01]]
[2016/5/15 11:25:29 : REVIEWED[User 02]]
[2016/5/15 14:31:03 : APPROVED[Admin 01]]

INFORMATION PROCESSING DEVICE, INFORMATION PROCESSING METHOD, AND INFORMATION PROCESSING PROGRAM

FIELD

The present invention relates to information processing device, an information processing method, and an information processing program for processing information based on a plurality of chromatograms obtained by analyzing a plurality of samples.

BACKGROUND

In order to quantify a target component contained in a sample, analysis using a high performance liquid chromatograph may be performed. For example, since mycotoxins having toxicity to humans or animals may be produced in food and beverages (e.g., see Patent Document 1 below), when each component of mycotoxin is analyzed as a target component by the high performance liquid chromatograph, each target component can be quantified based on the obtained chromatogram.

When the chromatogram is to be used for quantification of the target component, a calibration curve is prepared by measuring a standard sample of the target component, and based on the calibration curve and the chromatogram obtained by measuring the sample, the concentration of the target component contained in the sample is calculated. In this manner, the chromatogram is generally used for quantification of a target component and is not used for qualitative analysis of the target component.

Patent Document 1: Japanese Unexamined Patent Application Publication No. 2015-25680

SUMMARY

However, there are cases where only presence or absence of the target component in each sample is desired to be promptly confirmed, depending on the purpose of the analysis. For example, when each component of mycotoxin is contained in a sample extracted from a product such as food or a beverage, the product cannot be shipped, and hence a plurality of samples need to be screened in a short time by promptly and sequentially confirming only the presence or absence of each component of mycotoxin in a plurality of samples.

The present invention has been made in view of above circumstances, and an object thereof is to provide an information processing device, an information processing method, and an information processing program capable of promptly confirming presence or absence of target components in a plurality of samples.

(1) An information processing device according to the present invention is an information processing device for processing information based on a plurality of chromatograms obtained by analyzing a plurality of samples, and includes a determination processing unit and a list generation processing unit. The determination processing unit determines presence or absence of each of a plurality of target components in each sample based on the plurality of chromatograms. The list generation processing unit generates a list associating the plurality of target components with each sample and indicating the presence or absence of each of the plurality of target components in each sample determined by the determination processing unit.

With such a configuration, based on the plurality of chromatograms obtained by analyzing the plurality of samples, the presence or absence of each of the plurality of target components in each sample can be promptly confirmed, and a list indicating the result of the confirmation can be generated. Since the plurality of target components are associated with each sample in the list, it can be confirmed at a glance whether or not each target component is contained for each sample. Therefore, checking the list enables prompt confirmation of the presence or absence of the target components in the plurality of samples.

(2) The information processing device may further include a display unit and a display processing unit. The display processing unit causes the display unit to display the list generated by the list generation processing unit.

With such a configuration, the list can be displayed on the display unit and checked. Thus, checking the list displayed on the display unit enables prompt confirmation of the presence or absence of the target components in the plurality of samples.

(3) The determination processing unit may compare each parameter of the plurality of target components obtained from the plurality of chromatograms with a threshold corresponding to each parameter, to determine the presence or absence of each of the plurality of target components in each sample.

With such a configuration, it is possible to promptly determine the presence or absence of each of the plurality of target components in each sample only by comparing each parameter of the plurality of target components with the corresponding threshold. Hence a plurality of samples can be screened in a short time and a list indicating the results can be generated, thereby enabling prompt confirmation of the presence or absence of the target components in the plurality of samples.

(4) The information processing device may further include a threshold storage and an input reception unit. The threshold storage stores in advance a plurality of combinations of thresholds corresponding to the plurality of target components. The input reception unit receives a user's input operation to select a combination of thresholds stored in the threshold storage. In this case, the determination processing unit may read the combination of thresholds, selected by the input operation received by the input reception unit from the threshold storage, and compare each of the thresholds with each of parameters of the plurality of target components obtained from the plurality of chromatograms.

With such a configuration, arbitrary combinations can be selected from combinations of the thresholds stored in advance in the threshold storage, and the presence or absence of each of the plurality of target components in each sample can be determined using these thresholds. This can result in easy determination using a desired reference.

(5) The display processing unit may cause the display unit to display respective thresholds of the plurality of target components in association with the plurality of target components.

With such a configuration, not only the presence or absence of each of the plurality of target components in each sample but also the respective thresholds used for the determination are displayed on the display unit in association with the plurality of target components. The respective thresholds corresponding to the plurality of target components can thus be compared with the determination results, thus enabling more detailed analysis.

(6) The information processing device may further include a threshold change processing unit that changes each of the thresholds of the plurality of target components in accordance with a collection rate of each of the target components.

With such a configuration, it is possible to change each threshold in accordance with the collection rate of each target component and determine the presence or absence of each of the plurality of target components in each sample by using these thresholds. The presence or absence of a target component having a low collection rate may not be accurately determined even when a preset threshold is used, and hence, changing the threshold enables accurate determination.

(7) The display processing unit may cause the display unit to display respective collection rates of the plurality of target components in association with the plurality of target components.

With such a configuration, not only the presence or absence of each of the plurality of target components in each sample but also the respective collection rates for the plurality of target components are displayed on the display unit in association with the plurality of target components. The respective collection rates corresponding to the plurality of target components can thus be compared with the determination results, thus enabling more detailed analysis.

(8) The display processing unit may cause the presence or absence of the plurality of target components to be displayed in the list in different display modes between a target component determined not to be contained in the sample by the determination processing unit and a target component determined to be contained in the sample by the determination processing unit.

With such a configuration, the target component determined not to be contained in the sample and the target component determined to be contained in the sample can be easily distinguished from each other in the list, thereby enabling prompt confirmation of the presence or absence of the target components in the plurality of samples.

(9) The determination processing unit may compare each of the parameters of the plurality of target components obtained from the plurality of chromatograms with each of the plurality of thresholds, so as to determine the presence or absence of each of the plurality of target components in each sample on a plurality of levels. In this case, the display processing unit may cause the presence or absence of each of the plurality of target components in each sample determined by the determination processing unit to be displayed in the list in a different display mode for each of the levels.

With such a configuration, the presence or absence of each of the plurality of target components in each sample can be determined on a plurality of levels, and the determination result can be displayed in the list in a different display mode for each of the levels. Hence the determination result can be confirmed in the list in an easily understandable manner using the levels, thus enabling prompt confirmation of the presence or absence of the target components in the plurality of samples.

(10) The display processing unit may cause the display unit to display an individual determination result, indicating whether or not the determination processing unit has determined that each sample contains at least one target component, in association with each sample.

With such a configuration, when it is determined that each sample contains at least one target component, this can be easily confirmed for each sample as an individual determination result. Therefore, when it is desired to be screened whether or not at least one target component is contained in each sample, the screening can be performed in a short time by confirming the individual determination result for each sample.

(11) The display processing unit may cause the display unit to display an overall determination result indicating whether or not the determination processing unit has determined that at least one sample contains a target component.

With such a configuration, when it is determined that at least one of the plurality of samples contains a target component, this can be easily confirmed as an overall determination result. Therefore, when it is desired to screen whether or not at least one target component is contained in the plurality of samples, confirming the overall determination result enables the screening in a short time.

(12) The information processing device may further include a spectrum storage and a spectrum comparison processing unit. The spectrum storage stores a spectrum obtained by measuring in advance at least one of the plurality of target components as a spectrum library. The spectrum comparison processing unit compares the spectrum obtained based on the chromatogram of each sample with the spectrum library. In this case, the display processing unit may cause the display unit to display the comparison result by the spectrum comparison processing unit in association with each sample.

With such a configuration, not only the presence or absence of each of the plurality of target components in each sample but also the result of comparing the spectrum obtained from each sample with the spectrum library is also displayed on the display unit in association with each sample. A comparison can thus be made between the determination result for the presence or absence of each of the plurality of target components in each sample and the comparison result for the spectrums, thus enabling more detailed analysis.

(13) The list may be a table with each sample as a row and each of the plurality of target components as a column.

With such a configuration, even when the number of samples is large, only the number of rows in the list increases, and hence, sequentially checking each row in the list enables prompt confirmation of the presence or absence of each of the plurality of target components in each sample.

(14) The information processing device may further include a print processing unit that performs processing for printing the list.

With such a configuration, a list where each sample is a row and each of the plurality of target components is a column is printed and this list is used to enable prompt confirmation of the presence or absence of each of the plurality of target components in each sample. In particular, even when the number of samples is large, an increase in the number of rows in the list only increases the number of pages of the list, thereby facilitating confirmation of the presence or absence of each of the plurality of target components in each sample.

(15) The information processing device may further include an input reception unit that receives a user's input operation indicating that the list has been checked. In this case, the print processing unit may cause information of the input operation received by the input reception unit to be printed together with the list.

With such a configuration, the information of the user's input operation indicating that the list has been checked is printed together with the list, so that it is possible to achieve a function of an electronic signature. That is, before the list is printed, the user can check the list and perform a predetermined input operation for the electronic signature, and the result can be printed together with the list, thus eliminating the need for the user to circulate and check a printed matter.

(16) Each of the plurality of target components may be each component of mycotoxin Such a configuration enables prompt confirmation of the presence or absence of each component of mycotoxin in the plurality of samples. For example, when the presence or absence of each component of mycotoxin is to be confirmed for a large quantity of samples such as food and beverages, it is necessary to screen a plurality of samples in a short time. Even in such a case, according to the present invention, the list is checked to enable prompt confirmation of the presence or absence of each component of mycotoxin in the plurality of samples.

(17) The display processing unit may cause the display unit to display a total aflatoxins determination result, indicating whether or not the determination processing unit has determined that at least one component of total aflatoxins is contained in each sample, in association with each sample.

With such a configuration, when it is determined that at least one component of total aflatoxins, among the components of mycotoxin, is contained in each sample, this can be easily confirmed as a total aflatoxins determination result for each sample. Therefore, when it is desired to screen whether or not even one component of total aflatoxins is contained in each sample, confirming total aflatoxins determination result for each sample enables the screening in a short time.

(18) An information processing method according to the present invention is an information processing method for processing information based on a plurality of chromatograms obtained by analyzing a plurality of samples, the method including: a determination processing step, and a list generation processing step. The determination processing step determines presence or absence of each of a plurality of target components in each sample based on the plurality of chromatograms. The list generation processing step generates a list that associates the plurality of target components with each sample and indicates the presence or absence of each of the plurality of target components in each sample determined by the determination processing step.

(19) An information processing program according to the present invention is an information processing program for processing information based on a plurality of chromatograms obtained by analyzing a plurality of samples, the program causing a computer to function as a determination processing unit and a list generation processing unit. The determination processing unit determines presence or absence of each of a plurality of target components in each sample based on the plurality of chromatograms The list generation processing unit generates a list associating the plurality of target components with each sample and indicating the presence or absence of each of the plurality of target components in each sample determined by the determination processing unit.

According to the present invention, checking the list enables prompt confirmation of the presence or absence of the target components in the plurality of samples.

BRIEF DESCRIPTION OF THE DRAWINGS

FIG. 2 is a diagram showing a specific example of a list.

DETAILED DESCRIPTION

1. Configuration of Information Processing Device

Figure 1:
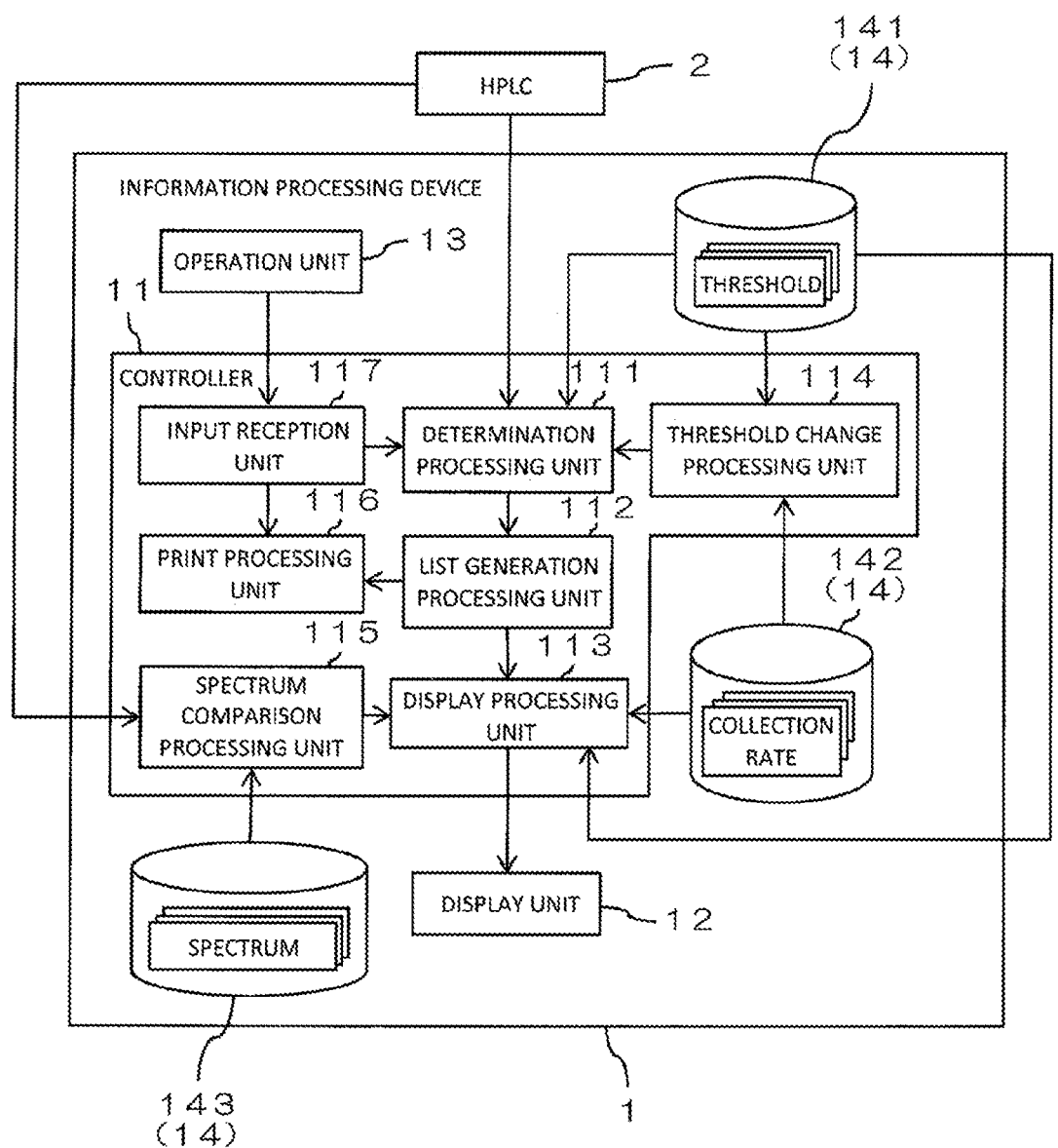
FIG. 1 is a block diagram showing a configuration example of an information processing device according to an embodiment of the present invention.

FIG. 1 is a block diagram showing a configuration example of an information processing device 1 according to an embodiment of the present invention. The information processing device 1 is connected to a high performance liquid chromatograph (HPLC) 2, for example, and processes data input from the HPLC 2. The information processing device 1 includes a controller 11, a display unit 12, an operation unit 13, a storage 14, and the like.

In the HPLC 2, by sequentially introducing a plurality of samples into a column (not shown), components contained in each sample are separated in the process of passing through the column. The components in the sample as thus separated are detected by a detector (not shown), whereby the analysis results for each sample are obtained as a plurality of chromatograms. The information processing device 1 processes information to be displayed on the display unit 12 based on a plurality of chromatograms obtained by analyzing a plurality of samples.

The controller 11 has a configuration including, for example, a central processing unit (CPU). By the CPU executing a program, the controller 11 functions as a determination processing unit 111, a list generation processing unit 112, a display processing unit 113, a threshold change processing unit 114, a spectrum comparison processing unit 115, a print processing unit 116, an input reception unit 117, and the like.

The display unit 12 is configured by, for example, a liquid crystal display, and various pieces of information such as a result of data processing by the controller 11 are displayed on a display screen. The operation unit 13 has a configuration including a keyboard and a mouse, for example, and can perform an input operation by a user operating the operation unit 13. The storage 14 is configured by, for example, a random access memory (RAM), a hard disk, and the like.

The determination processing unit 111 determines the presence or absence of each of a plurality of target components in each sample based on a plurality of chromatograms obtained by analyzing a plurality of samples in the HPLC 2. Specifically, the determination processing unit 111 compares each of parameters of the plurality of target components obtained from the plurality of chromatograms with a threshold corresponding to each target component. The threshold corresponding to each target component is preset and stored in the threshold storage 141 allocated to the storage 14. Examples of the above parameter include detection intensity, a concentration, and an area value of each target component in the HPLC 2, but these are not restrictive.

The target component in the present embodiment is each component of mycotoxin, such as four components (AFB1, AFB2, AFG1, AFG2) of total aflatoxins, zearalenone (ZON), oculatoxin (OTA), deoxynivalenol (DON), and nivalenol (NIV). However, the target component is not limited to each of the above components.

Based on the determination result of the determination processing unit 111, the list generation processing unit 112 generates a list indicating the presence or absence of each of a plurality of target components in each sample. This list is, for example, a matrix table with each sample as a row and each of a plurality of target components as a column, and a plurality of target components are associated with each sample. In the list, for each sample, the presence or absence of each of the plurality of target components is displayed in association with each target component.

The display processing unit 113 controls display on the display screen of the display unit 12. In the present embodiment, the list generated by the list generation processing unit 112 is displayed on the display unit 12 by the display processing unit 113. In this manner, the presence or absence of each of the plurality of target components in each sample can be promptly confirmed based on the plurality of chromatograms obtained by analyzing the plurality of samples, and the result can be displayed in a list on the display unit 12.

In particular, in the present embodiment, it is possible to promptly determine the presence or absence of each of the plurality of target components in each sample only by comparing each parameter of the plurality of target components with the corresponding threshold. Hence the plurality of samples can be screened in a short time and a list indicating the results can be displayed on the display unit 12, thereby enabling prompt confirmation of the presence or absence of the target components in the plurality of samples.

For example, when the presence or absence of each component of mycotoxin is to be confirmed for a large quantity of samples such as food and beverages, it is necessary to screen a plurality of samples in a short time. Even in such a case, in the present embodiment, the list displayed on the display unit 12 is checked to enable prompt confirmation of the presence or absence of each component of mycotoxin in the plurality of samples.

The threshold change processing unit 114 changes each of thresholds of a plurality of target components stored in advance in the threshold storage 141 and provides the changed threshold to the determination processing unit 111. For example, the presence or absence of a target component having a low collection rate may not be accurately determined even when the threshold stored in the threshold storage 141 is used as it is. Therefore, the threshold change processing unit 114 changes the threshold to a value smaller than a preset value for the target component with a collection rate being smaller than a certain value (e.g., 50%). As thus described, changing each threshold in accordance with the collection rate of each target component enables accurate determination. The collection rates corresponding to the respective target components are stored in advance in the collection rate storage 142 allocated to the storage 14.

In the present embodiment, for a plurality of chromatograms obtained by analyzing the plurality of samples in the HPLC 2, there is obtained a spectrum which is made up of three-dimensional data taking detection intensity, a wavelength, and time as axes. In the spectrum storage 143 allocated to the storage 14, a spectrum obtained by measuring the target component in advance is stored as a spectrum library. The spectrum library is not limited to such a configuration as to store spectrums for all target components, but the spectrum library may only store a spectrum for at least one of the plurality of target components (e.g., deoxynivalenol and nivalenol).

The spectrum comparison processing unit 115 compares the spectrum obtained based on the chromatogram of each sample with the spectrum library. Specifically, the similarity between the spectrum obtained by measuring each sample and the spectrum stored as the spectrum library in the spectrum storage 143 is calculated as a comparison result. Since the algorithm for calculating the similarity of spectrums is known, the description thereof will be omitted.

The print processing unit 116 performs processing for printing the list generated by the list generation processing unit 112. Through the processing of the print processing unit 116, the list is output as a printed matter from a printer (not shown). Therefore, the list indicating the presence or absence of each of the plurality of target components in each sample can be confirmed not only on the display screen of the display unit 12 but also with the printed matter.

The input reception unit 117 receives the user's input operation on the operation unit 13. The user's input operations include, for example, an input operation (operation of a check button, etc.) indicating that the user has checked the list displayed on the display unit 12. The print processing unit 116 can cause the information (the list has been checked, etc.) of the input operation received by the input reception unit 117 to be printed together with the list. However, the input operation on the operation unit 13 is not restrictive, but the input operation on another terminal connected to the information processing device 1 via a network may be received by the input reception unit 117.

In the present embodiment, a plurality of combinations of thresholds corresponding to a plurality of target components are stored in advance in the threshold storage 141. The combination of these thresholds may be preset as, for example, a fixed value in accordance with the criteria for each country or each region, or may be set to arbitrary value by the user operating the operation unit 13. By operating the operation unit 13 in advance before the start of the analysis, the user can select any one of the threshold combinations stored in the threshold storage 141.

When the combination of thresholds is selected as thus described, the user's input operation is received by the input reception unit 117. In this case, the determination processing unit 111 reads the combination of the thresholds selected by the input operation received by the input reception unit 117 from the threshold storage 141, and compares these thresholds with the respective parameters of a plurality of target components obtained from a plurality of chromatograms. This makes it possible to select arbitrary combinations from the combinations of the thresholds stored in advance in the threshold storage 141 and determine the presence or absence of each of the plurality of target components in each sample by using these thresholds. This can result in easy determination using a desired reference.

2. Specific Examples of the List

FIG. 2 is a diagram showing a specific example of a list 200. The list 200 is a table with each sample as a row and each target component as a column, and indicates the presence or absence of each target component in each of nine samples, which are four components (AFB1, AFB2, AFG1, AFG2) of total aflatoxins, zearalenone (ZON), oculatoxin (OTA), deoxynivalenol (DON), and nivalenol (NW).

In this example, a target component determined not to be contained in each sample is indicated in association with a symbol "○" and characters "N.D." On the other hand, a target component determined to be contained in each sample is indicated in association with a symbol "×" or "Δ" and a value of a parameter (e.g., concentration).

As described above, since a plurality of target components are associated with each sample in the list 200, it can be confirmed at a glance whether or not each target component is contained for each sample. Thus, checking the list 200 displayed on the display unit 12 enables prompt confirmation of the presence or absence of the target components in the plurality of samples.

In particular, since the list 200 is a table with each sample as a row and each of a plurality of target components as a column, even when the number of samples is large, only the number of rows in the list 200 increases. Thus, sequentially checking each row in the list 200 enables prompt confirmation of the presence or absence of each of the plurality of target components in each sample.

In addition, as described above, the target component ("○" and "N.D." are displayed) determined not to be contained in the sample and the target component (the symbol "×" or "Δ" and the parameter are displayed) determined to be contained in the sample are displayed in the list 200 in display modes in which the presence or absence of each of the plurality of target components are different. This facilitates distinguishing between the target component determined not to be contained in the sample and the target component determined to be contained in the sample in the list 200, thereby enabling prompt confirmation of the presence or absence of the target component in the plurality of samples.

The list 200 includes a quantitative lower limit display section 201, a reference value display section 202, a collection rate display section 203, a total aflatoxins determination display section 204, an individual determination display section 205, and the like. Further, together with the list 200, an overall determination display section 206, an analysis information display section 207, and the like are also displayed on the display unit 12.

The quantitative lower limit display section 201 constitutes one row in the list 200 and displays a quantitative lower limit as a first threshold in association with each of the plurality of target components. The quantitative lower limit is a threshold for, for example, distinguishing between a parameter (e.g., concentration) based on a target component and a parameter based on noise, and a target component with its parameter being equal or larger than the quantitative lower limit is determined to be contained in the sample by the determination processing unit 111.

The reference value display section 202 constitutes one row in the list 200 and displays a set value of a reference value as a second threshold in association with each of the plurality of target components. The reference value is set in advance for each target component as an allowable upper limit of a content of a target component. In the present embodiment, a plurality of combinations of the reference values (thresholds) are stored in the threshold storage 141, and the combination of the thresholds selected by the user operating the operation unit 13 in advance before the start of analysis is displayed in the reference value display section 202. The reference value is a value larger than the quantitative lower limit, and a target component with its parameter being equal or larger than the reference value is not only determined to be contained in the sample by the determination processing unit 111, but also determined to be "Fail". Meanwhile, a target component with its parameter being equal to or larger than the quantitative lower limit and is smaller than the reference value is determined as "Caution". Further, a target component with its parameter being smaller than the quantitative lower limit is determined as "Pass".

As described above, the determination processing unit 111 compares each of the parameters of the plurality of target components obtained from the plurality of chromatograms with each of the plurality of thresholds (quantitative lower limit and reference value), so as to determine the presence or absence of each of the plurality of target components in each sample on a plurality of levels. Of the display corresponding to each target component in the list 200, the display of "○" and "N.D." means that the parameter is smaller than the quantitative lower limit (Pass). In contrast, the display of "×" and the parameter means that the parameter is equal to or larger than the reference value (Fail). Further, the display of "Δ" and the parameter means that the parameter is equal to or larger than the quantitative lower limit and is smaller than the reference value (Caution).

As described above, in the present embodiment, each threshold (quantitative lower limit and reference value) of the plurality of target components is displayed on the display unit 12 in association with each of the plurality of target components. That is, not only the presence or absence of each of the plurality of target components in each sample but also each threshold used for the determination is also displayed on the display unit 12 in association with each of the plurality of target components. The respective thresholds corresponding to the plurality of target components can thus be compared with the determination results, thus enabling more detailed analysis.

In the present embodiment, the presence or absence of each of the plurality of target components in each sample is displayed in the list 200 in a different display mode for each level (Pass, Caution, and Fail) in accordance with the plurality of thresholds (quantitative lower limit and reference value). Hence the determination result can be checked in the list 200 in an easily understandable manner using the levels, thus enabling prompt confirmation of the presence or absence of the target components in the plurality of samples.

However, the respective thresholds for the plurality of target components are not limited to the configuration displayed as a part of the list 200 as the quantitative lower limit display section 201 and the reference value display section 202. That is, the quantitative lower limit display section 201 and the reference value display section 202 may be displayed on the display unit 12 separately from the list 200.

The collection rate display section 203 constitutes one row in the list 200 and displays respective collection rates for the plurality of target components stored in the collection rate storage 142 in association with the plurality of target components. The respective collection rates corresponding to the plurality of target components can thus be compared with the determination results, thus enabling more detailed analysis. In this example, a collection rate of soft wheat flour is displayed in the collection rate display section 203, but this is not restrictive. Further, the collection rate display section 203 is not limited to such a configuration as to be displayed in a part of the list 200, and may be displayed on the display unit 12 separately from the list 200.

The total aflatoxins determination display section 204 constitutes one column in the list 200 and displays total aflatoxins determination result in association with each sample. The total aflatoxins determination result indicates whether or not each sample contains at least one component of the four components (AFB1, AFB2, AFG1, AFG2) of total aflatoxins. Specifically, for a sample in which the determination result for at least one component of total aflatoxins is "Fail", the total aflatoxins determination display section 204 displays "×" and the parameter (the total value of each parameter of total aflatoxin). When the determination result that at least one component of total aflatoxins is "Caution" and there is no component determined as "Fail", the total aflatoxins determination display section 204 displays "Δ" and the parameter (total value of each parameter of total aflatoxins). When all the determination results for the respective components of total aflatoxins are "Pass", the total aflatoxins determination display section 204 displays "○" and "N.D."

As thus described, when it is determined that at least one component of total aflatoxins, among the components of mycotoxin, is contained in each sample, this can be easily confirmed for each sample in the total aflatoxins determination display section 204. Therefore, when it is desired to screen whether or not even one component of total aflatoxins is contained in each sample, the screening can be performed in a short time by checking the total aflatoxins determination display section 204.

In particular, in the present embodiment, whether or not at least one component of total aflatoxins is contained in each sample is displayed in the total aflatoxins determination display section 204 in a different display mode for each level (Pass, Caution, and Fail) corresponding to each of the plurality of thresholds (quantitative lower limit and reference value). Hence the determination result for total aflatoxins can be confirmed in the total aflatoxins determination display section 204 in an easily understandable manner using the levels. However, the total aflatoxins determination display section 204 is not limited to a configuration that is displayed in a part of the list 200, and may be displayed on the display unit 12 separately from the list 200.

The individual determination display section 205 constitutes one column in the list 200 and displays an individual determination result in association with each sample. The individual determination result indicates whether or not each sample contains at least one target component. Specifically, for a sample in which the determination result for at least one target component of all the target components is "Fail", the individual determination display section 205 displays "Fail". When the determination result for at least one target component of all the target components is "Caution" and there is no target component determined to be "Fail", the individual determination display section 205 displays "Caution". When the determination result for all the target components is "Pass", the individual determination display section 205 displays "Pass". In this case, the determination results may be displayed in different display modes such as color-coded modes with red for "Fail" and yellow for "Caution".

As described above, when it is determined that each sample contains at least one target component, this can be easily confirmed for each sample in the individual determination display section 205. Therefore, when it is desired to screen whether or not at least one target component is contained in each sample, the screening can be performed in a short time by checking the individual determination display section 205.

In particular, in the present embodiment, whether or not each sample contains at least one target component is displayed in the individual determination display section 205 in a different display mode for each level (Pass, Caution, and Fail) in accordance with the plurality of thresholds (quantitative lower limit and reference value). Hence an individual determination result for each sample can be confirmed in the individual determination display section 205 in an easily understandable manner using the levels. However, the individual determination display section 205 is not limited to such a configuration as to be displayed in a part of the list 200, and may be displayed on the display unit 12 separately from the list 200.

The overall determination display section 206 displays the overall determination result separately from the list 200. The overall determination result indicates whether or not the target component has been determined to be contained in at least one sample among all the samples. Specifically, when the individual determination result for at least one sample out of all the samples is "Fail", the overall determination display section 206 displays "Fail". When the individual determination result for at least one sample of all the samples is "Caution" and there is no sample determined to be "Fail", the overall determination display section 206 displays "Caution". When the individual determination result for all the target samples is "Pass", the overall determination display section 206 displays "Pass". In this case, the determination results may be displayed in different display modes such as color-coded modes with red for "Fail" and yellow for "Caution".

As thus described, when it is determined that at least one of the plurality of samples contains a target component, this can be easily confirmed in the overall determination display section 206. Therefore, when it is desired to screen whether or not at least one target component is contained in the plurality of samples, checking the overall determination display section 206 enables the screening in a short time.

In particular, in the present embodiment, whether or not at least one of the plurality of samples contains a target component is displayed in the overall determination display section 206 in a different display mode for each level (Pass, Caution, and Fail) in accordance with the plurality of thresholds (quantitative lower limit and reference value). Hence an overall determination result for all the samples can be confirmed in the overall determination display section 206 in an easily understandable manner using the levels. However, the overall determination display section 206 is not limited to such a configuration as to be displayed separately from the list 200, and may be displayed on the display unit 12 in a part of the list 200.

The analysis information display section 207 is displayed separately from the list 200 and displays information on analysis. The information on the analysis includes, for example, information such as a device name, an analyst, an analysis date and time, but these are not restrictive. However, the analysis information display section 207 is not limited to such a configuration as to be displayed on the display unit 12 separately from the list 200, and may be displayed in a part of the list 200.

The list 200 displayed on the display unit 12 as shown in FIG. 2 can be printed by the processing of the print processing unit 116. Hence the list 200 with each sample as a row and each of the plurality of target components as a column is printed and the list 200 is used to enable prompt confirmation of the presence or absence of each of the plurality of target components in each sample. In particular, even when the number of samples is large, an increase in the number of rows in the list 200 only increases the number of pages of the list 200 to be printed, thereby facilitating confirmation of the presence or absence of each of the plurality of target components in each sample.

Further, in the present embodiment, information of the input operation (input operation information 210) indicating that the user has confirmed the list 200 displayed on the display unit 12 is printed together with the list 200. The input operation information 210 includes not only information that the contents of the list 200 are simply checked but also information that the contents of the list 200 have been reviewed, information that the contents of the list 200 have been approved, and the like. Further, the input operation information 210 may include identification information of a user who has performed an input operation to "confirm", "review", "approve", or the like and the date and time when the input operation was performed, and the like.

As thus described, the information (input operation information 210) of the user's input operation indicating that the list 200 has been checked is printed together with the list 200, so that it is possible to achieve a function of an electronic signature. That is, before the list 200 is printed, the user can check the list and perform a predetermined input operation for the electronic signature, and the result can be printed together with the list 200, thus eliminating the need for the user to circulate and check a printed matter.

3. First Modification of List

Figure 3:
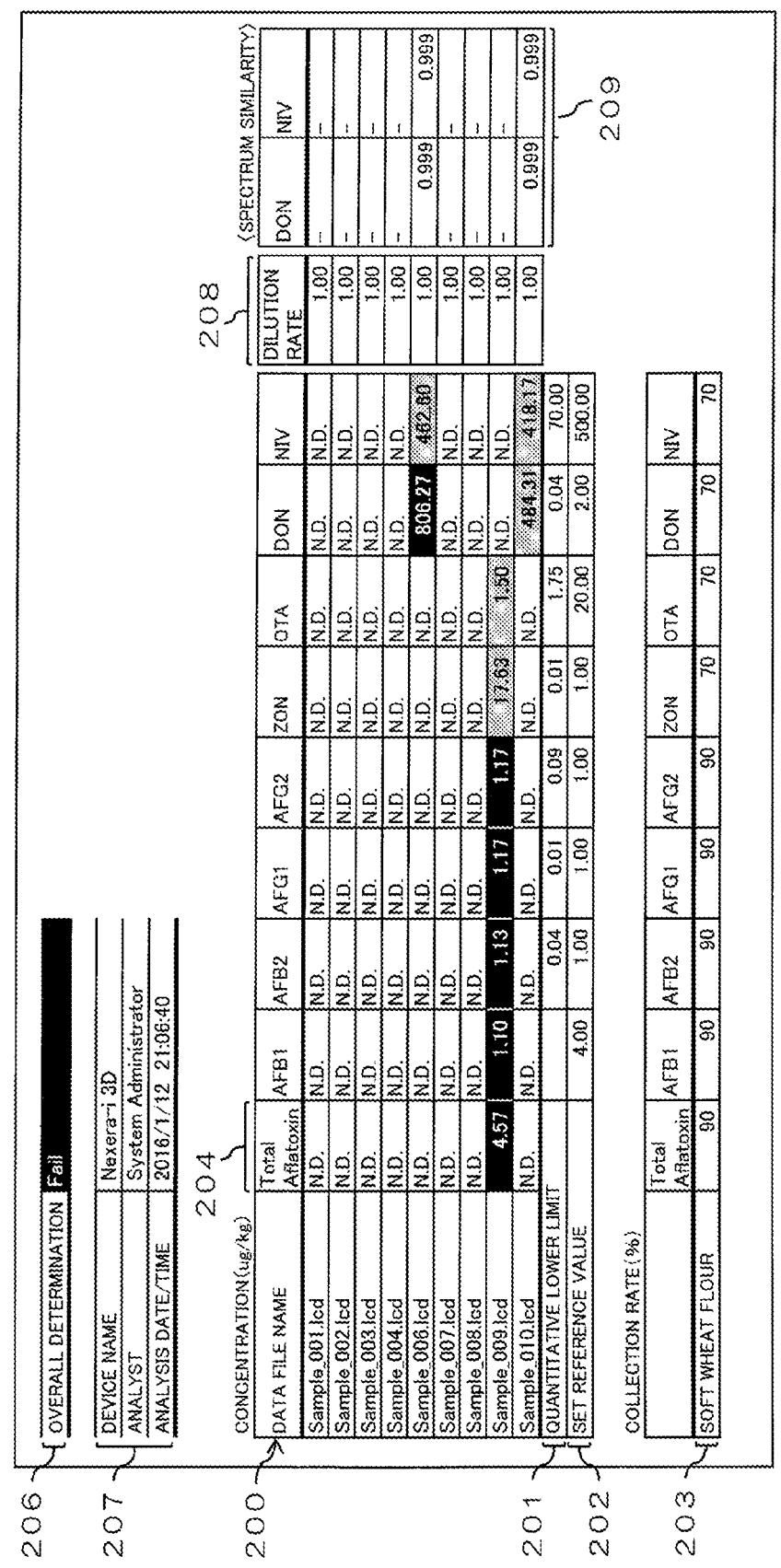
FIG. 3 is a diagram showing a first modification of the list.

FIG. 3 is a diagram showing a first modification of the list 200. As in the case of FIG. 2, the list 200 is a table with each sample as a row and each target component as a column, and indicates the presence or absence of each target component in each of nine samples which are four components (AFB1, AFB2, AFG1, AFG2) of total aflatoxins, zearalenone (ZON), oculatoxin (OTA), deoxynivalenol (DON), and nivalenol (NW). Hereinafter, only portions different from the list 200 of FIG. 2 will be described, and the same portions as in the list 200 of FIG. 2 will be provided with the same reference numerals and the description thereof will be omitted.

In this example, a target component determined not to be contained in each sample (Pass) is indicated in association with the characters "N.D." On the other hand, a target component determined to be contained in each sample (Fail or Caution) is indicated in association with a value of a parameter (e.g., concentration). In this case, the determination results may be displayed in different display modes such as color-coded modes with red for "Fail" and yellow for "Caution".

The collection rate display section 203 is displayed separately from the list 200 and displays the collection rates for a plurality of target components. However, the collection rate display section 203 is not limited to such a configuration as to be separated from the list 200 and displayed on the display unit 12, and may be displayed in a part of the list 200.

The total aflatoxins determination display section 204 constitutes one column in the list 200 and displays total aflatoxins determination result in association with each sample. Specifically, for a sample in which the determination result for at least one component of total aflatoxins is "Fail", the parameter (total value of each parameter of total aflatoxins) is displayed in the total aflatoxins determination display section 204 and color-coded with red or the like. When the determination result that at least one component of total aflatoxins is "Caution" and there is no component determined as "Fail", the parameter (total value of each parameter of total aflatoxins) is displayed in the total aflatoxins determination display section 204 and color-coded with yellow or the like. When all the determination results for the respective components of total aflatoxins are "Pass", the total aflatoxins determination display section 204 displays "N.D."

In this example, together with the list 200, a dilution rate display section 208, a spectrum similarity display section 209, and the like are displayed on the display unit 12. The dilution rate display section 208 and the spectrum similarity display section 209 are not limited to such a configuration as to be displayed on the display unit 12 separately from the list 200, and may be displayed in a part of the list 200.

The dilution rate display section 208 displays a dilution rate of each sample in association with each sample. A parameter (e.g., concentration) of the target component in each sample is calculated based on the dilution rate of each sample.

The spectrum similarity display section 209 causes the display unit 12 to display the comparison result by the spectrum comparison processing unit 115 in association with each sample. Specifically, the similarity (spectral similarity) between the spectrum obtained by measuring each sample and the spectrum stored as the spectrum library in the spectrum storage 143 is calculated by the spectrum comparison processing unit 115 as a comparison result, and the spectral similarity is displayed in the spectrum similarity display section 209 for each target component. In this example, the spectral similarities of deoxynivalenol (DON) and nivalenol (NIV) are displayed in the spectrum similarity display section 209, but this is not restrictive, and the spectral similarities of other target components may be displayed.

As thus described, in the example of FIG. 3, not only the presence or absence of each of the plurality of target components in each sample but also the result for comparing the spectrum obtained from each sample with the spectrum library is also displayed on the display unit 12 in association with each sample. A comparison can thus be made between the determination result for the presence or absence of each of the plurality of target components in each sample and the comparison result for the spectrums, thus enabling more detailed analysis.

4. Second Modification of List

Figure 4:
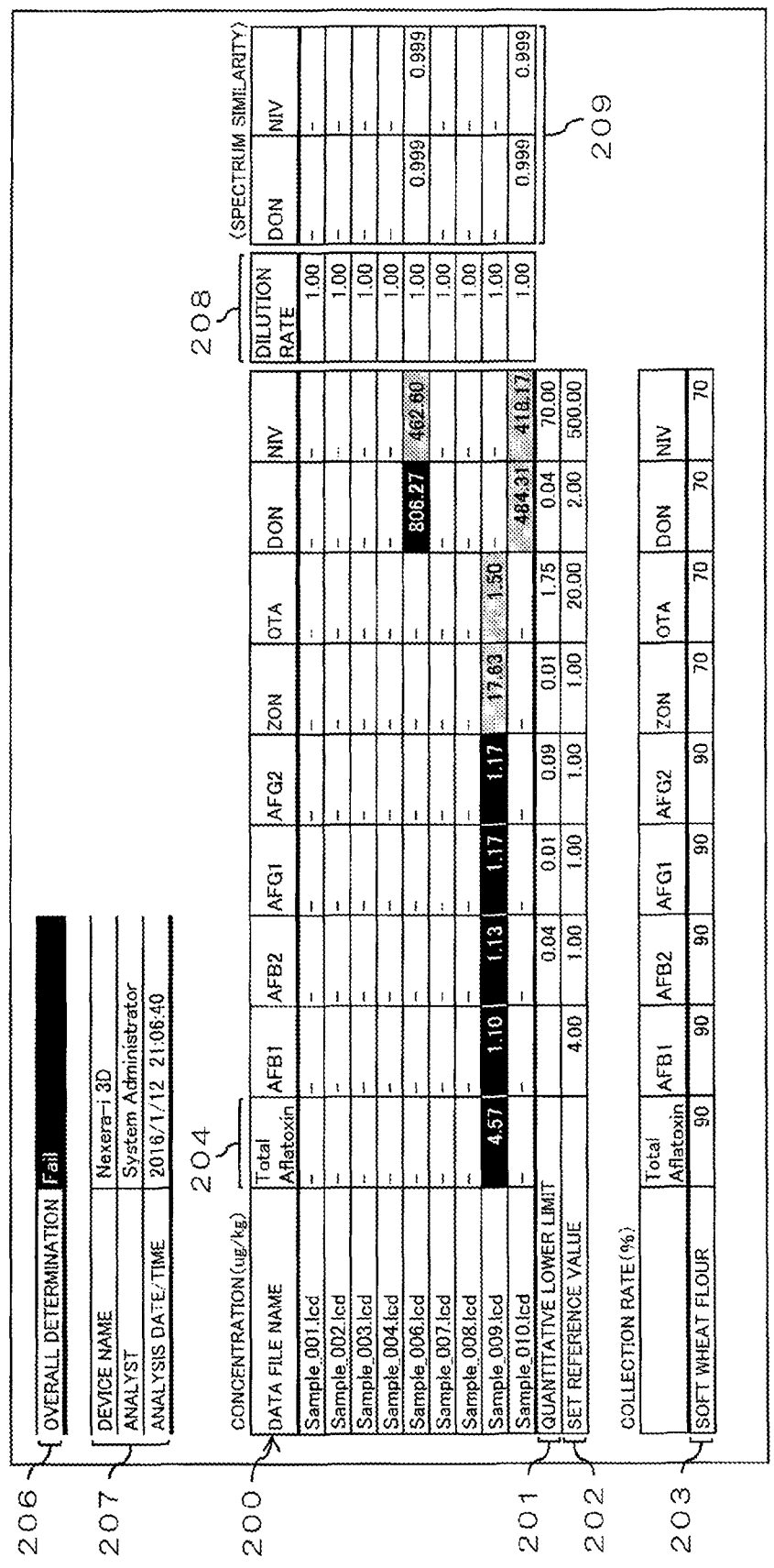
FIG. 4 is a diagram showing a second modification of the list.

FIG. 4 is a diagram showing a second modification of the list 200. As in the case of FIG. 3, the list 200 is a table with each sample as a row and each target component as a column, and indicates the presence or absence of each target component in each of nine samples which are four components (AFB1, AFB2, AFG1, AFG2) of total aflatoxins, zearalenone (ZON), oculatoxin (OTA), deoxynivalenol (DON), and nivalenol (NIV). Hereinafter, only portions different from the list 200 of FIG. 3 will be described, and the same portions as in the list 200 of FIG. 3 will be provided with the same reference numerals and the description thereof will be omitted.

In this example, a symbol "-" is shown in association with a target component determined not to be contained in each sample (Pass). On the other hand, a target component determined to be contained in each sample (Fail or Caution) is indicated in association with a value of a parameter (e.g., concentration). In this case, the determination results may be displayed in different display modes such as color-coded modes with red for "Fail" and yellow for "Caution".

As described above, various changes as shown in FIGS. 2 to 4 can be made to the display mode of the list 200. However, the display mode of the list 200 is not limited to the display mode as shown in FIGS. 2 to 4. For example, on the display unit 12, at least one of the quantitative lower limit display section 201, the reference value display section 202, the collection rate display section 203, the total aflatoxins determination display section 204, the individual determination display section 205, the overall determination display section 206, the analysis information display section 207, the dilution rate display section 208, and the spectrum similarity display section 209 may be displayed in an arbitrary manner in a part of the list 200 or separately from the list 200.

5. Processing by Controller

Figure 5:
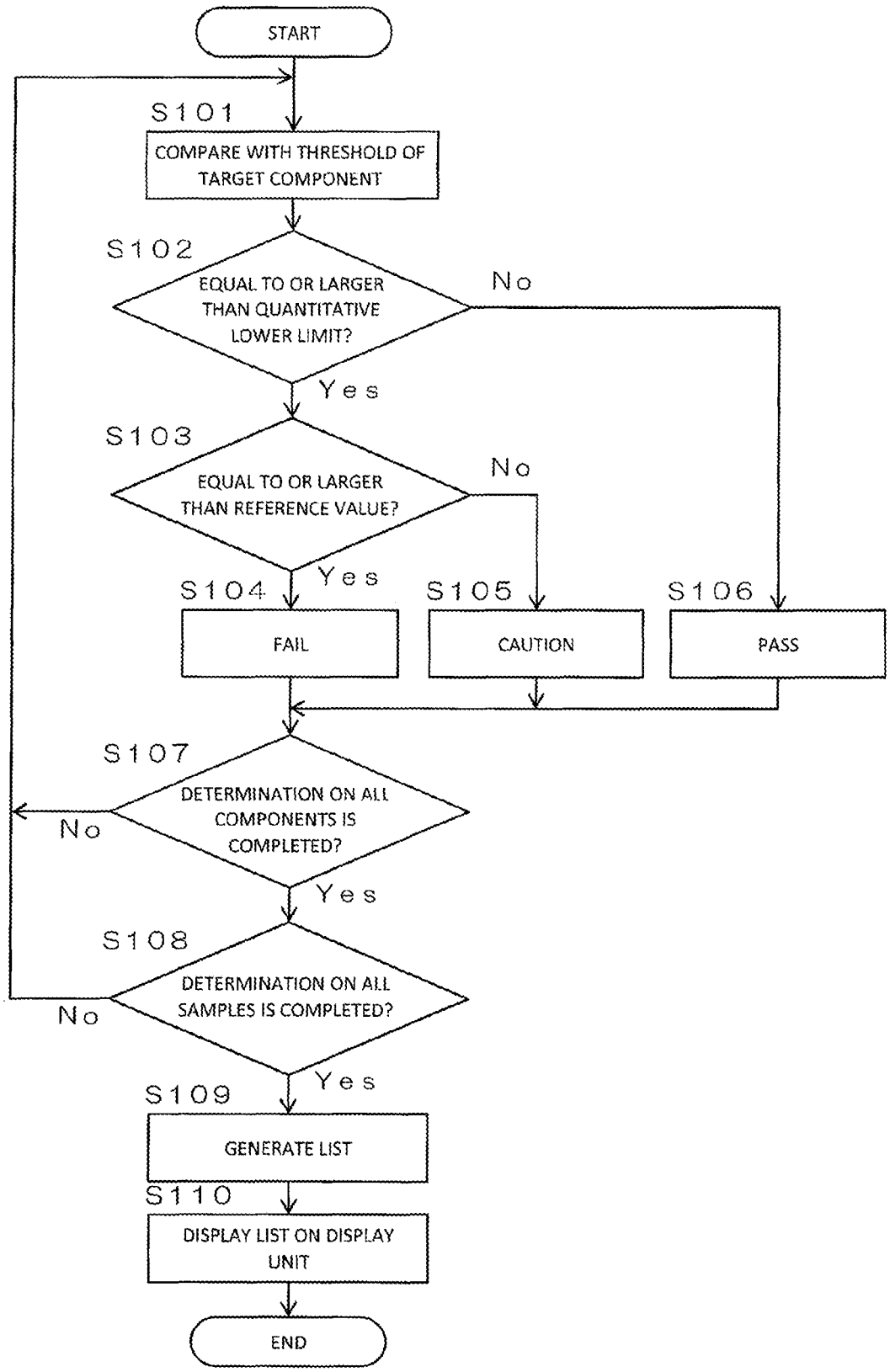
FIG. 5 is a flowchart showing an example of processing by a controller.

FIG. 5 is a flowchart showing an example of processing by the controller 11. The controller 11 repeatedly executes processing of Steps S101 to S107 (determination processing step) of FIG. 5 for all the samples to generate the list 200 indicating the presence or absence of the target components in all the samples.

Specifically, first, based on a chromatogram obtained by analyzing a first sample, the determination processing unit 111 sequentially compares parameters for the respective target components with thresholds corresponding to the respective target components (step S101). Then, as for a target component with its parameter being smaller than the quantitative lower limit (No in step S102), the target component is determined as "Pass" (step in S106).

On the other hand, for a target component with its parameter being equal to or larger than the quantitative lower limit (Yes in step S102), it is determined whether or not the parameter is equal to or larger than the reference value (step S103). Then, for a target component with its parameter being equal to or larger than the reference value (Yes in step S103), the target component is determined to be "Fail" (step S104). In contrast, for a target component with its parameter being equal to or larger than the quantitative lower limit and is smaller than the reference value (No in step S103), the target component is determined as "Caution" (step S105).

The processing in steps S101 to S106 as described above is repeatedly performed for all target components for the first sample. When the determination of all target components is completed (Yes in step S107), the processing of steps S101 to S107 are repeated based on the chromatogram obtained by analyzing a second sample. In this manner, the determination processing on each sample is sequentially performed, and when the determination processing on all the samples is completed (Yes in step S108), the list generation processing unit 112 generates the list 200 based on the determination result (step S109: list generation processing step).

The generated list 200 is displayed on the display unit 12 by the display processing unit 113 (step S110: display processing step). Although not shown in FIG. 5, when an operation for printing the list 200 displayed on the display unit 12 is performed, processing for printing the list 200 may be performed by the print processing unit 116.

6. Modifications

In the above embodiment, the case has been described in which the list 200 is a matrix table with each sample as a row and each of a plurality of target components as a column. However, such a configuration is not restrictive, and the list can be displayed in another arbitrary display mode as long as it is a list indicating the presence or absence of each of a plurality of target components in each sample, determined by the determination processing unit 111.

Further, the list is not limited to such a configuration as to be displayed on the display unit 12 by the display processing unit 113. For example, the list generated by the list generation processing unit 112 may be merely printed by the print processing unit 116 without being displayed on the display unit 12, or the data of the list may be transmitted from the information processing device 1 to another apparatus.

The data of a plurality of chromatograms to be input into the information processing device 1 is not limited to a configuration to be input from a liquid chromatograph such as the HPLC 2, and may be input from a gas chromatograph, for example. In addition, the data of a plurality of chromatograms input into the information processing device 1 may be temporarily stored into the storage 14 and may be read out in a predetermined order to generate a list. In this case, the order of reading data of a plurality of chromatograms from the storage 14 may be set by operation of the operation unit 13, or the like.

Instead of providing the information processing device 1 incorporating the program as in the above embodiment, it is also possible to provide a program (information processing program) for causing a computer to function as the information processing device 1. In this case, the program may be provided in a state stored in a storage medium, or may be provided such that the program itself is provided via wired communication or wireless communication.

The invention claimed is:

1. An information processing device for processing information based on a plurality of chromatograms obtained by analyzing a plurality of samples, the device comprising:
   a determination processing section determining presence or absence of each of a plurality of target components, each being a component of mycotoxin, in each sample based on the plurality of chromatograms obtained by analyzing each sample; and
   a list generation processing section generating a list associating the plurality of target components, each being the component of mycotoxin, with each sample and indicating both the presence and absence of each of the plurality of target components, each being the component of mycotoxin, in each sample determined by the determination processing section,
   wherein the list is a table which includes names of the plurality of samples and each of the plurality of names of target components, wherein the presence or absence of each of the plurality of target components is indicated based on a predetermined threshold specific to each target component,
   wherein the determination processing section compares each parameter of the plurality of target components obtained from the plurality of chromatograms with the threshold corresponding to each parameter, to determine the presence or absence of each of the plurality of target components in each sample.

2. The information processing device according to claim 1, further comprising:
   a display processing section causing a display section to display the list generated by the list generation processing section.

3. The information processing device according to claim 1, further comprising:
   a threshold storage that stores in advance a plurality of combinations of thresholds corresponding to the plurality of target components; and
   an input reception section receiving a user's input operation to select a combination of thresholds stored in the threshold storage,
   wherein the determination processing section reads the combination of thresholds, selected by the input operation received by the input reception section from the threshold storage, and compares each of the thresholds with each of parameters of the plurality of target components obtained from the plurality of chromatograms.

4. The information processing device according to claim 1, further comprising:
   a display processing section causing-display section to display the list generated by the list generation processing section, wherein the display processing section causes the display section to display respective thresholds of the plurality of target components in association with the plurality of target components.

5. The information processing device according to claim 1, further comprising a threshold change processing section changing each of the thresholds of the plurality of target components in accordance with a collection rate of each of the target components.

6. The information processing device according to claim 2, wherein the display processing section causes the display section to display respective collection rates of the plurality of target components in association with the plurality of target components.

7. The information processing device according to claim 2, wherein the display processing section causes the presence or absence of the plurality of target components to be displayed in the list in different display modes between a target component determined not to be contained in the sample by the determination processing section and a target component determined to be contained in the sample by the determination processing section.

8. The information processing device according to claim 2, wherein
   the determination processing section compares each of the parameters of the plurality of target components obtained from the plurality of chromatograms with each of the plurality of thresholds, so as to determine the presence or absence of each of the plurality of target components in each sample on a plurality of levels, and
   the display processing section causes the presence or absence of each of the plurality of target components in each sample determined by the determination processing section to be displayed in the list in a different display mode for each of the levels.

9. The information processing device according to claim 2, wherein the display processing section causes the display section to display an individual determination result, indicating whether or not the determination processing section has determined that each sample contains at least one target component, in association with each sample.

10. The information processing device according to claim 2, wherein the display processing section causes the display section to display an overall determination result indicating whether or not the determination processing section has determined that at least one sample contains a target component.

11. The information processing device according to claim 2, further comprising:
    a spectrum storage that stores a spectrum obtained by measuring in advance at least one of the plurality of target components as a spectrum library; and
    a spectrum comparison processing section comparing the spectrum obtained based on the chromatogram of each sample with the spectrum library,
    wherein the display processing section causes the display section to display a comparison result by the spectrum comparison processing section in association with each sample.

12. The information processing device according to claim 1, wherein the list is a table with each sample as a row and each of the plurality of target components as a column.

13. The information processing device according to claim 12, further comprising a print processing section performing processing for printing the list.

14. The information processing device according to claim 13, further comprising an input reception section receiving a user's input operation indicating that the list has been checked,
    wherein the print processing section causes information of the input operation received by the input reception section to be printed together with the list.

15. The information processing device according to claim 1, further comprising:
    a display processing section causing a display section to display the list generated by the list generation processing section,
    wherein the display processing section causes the display section to display a total aflatoxins determination result, indicating whether or not the determination processing section has determined that at least one component of total aflatoxins is contained in each sample, in association with each sample.

16. An information processing method for processing information based on a plurality of chromatograms obtained by analyzing a plurality of samples, the method comprising:
    a determination processing step of determining presence or absence of each of a plurality of target components, each being a component of mycotoxin, in each sample based on the plurality of chromatograms obtained by analyzing each sample; and
    a list generation processing step of generating a list that associates the plurality of target components, each being the component of mycotoxin, with each sample and indicates both the presence and absence of each of the plurality of target components, each being the component of mycotoxin, in each sample determined by the determination processing step,
    wherein the list is a table which includes names of the plurality of samples and each of the plurality of target components and the presence or absence of each of the plurality of target components is indicated based on a predetermined threshold specific to each target component,
    wherein the determination processing step compares each parameter of the plurality of target components obtained from the plurality of chromatograms with the threshold corresponding to each parameter, to determine the presence or absence of each of the plurality of target components in each sample.

17. Non-transitory computer readable medium storing an information processing program for processing information based on a plurality of chromatograms obtained by analyzing a plurality of samples, the program causing a computer to function as:
    a determination processing section that determines presence or absence of each of a plurality of target components, each being a component of mycotoxin, in each sample based on the plurality of chromatograms obtained by analyzing each sample; and
    a list generation processing section that generates a list associating the plurality of target components, each being the component of mycotoxin, with each sample and indicating both the presence and absence of each of the plurality of target components, each being the component of mycotoxin, in each sample determined by the determination processing section,
    wherein the list is a table which includes names of the plurality of samples and each of the plurality of target components and wherein the presence or absence of each of the plurality of target components is indicated based on a predetermined threshold specific to each target component, wherein the determination processing section compares each parameter of the plurality of target components obtained from the plurality of chromatograms with the threshold corresponding to each parameter, to determine the presence or absence of each of the plurality of target components in each sample.

* * * * *